United States Patent [19]

Shattil et al.

[11] Patent Number: 5,169,836
[45] Date of Patent: Dec. 8, 1992

[54] INHIBITORS OF PLATELET BINDING

[75] Inventors: Sanford J. Shattil, Narberth; Rebecca A. Taub; Paul A. Friedman, both of Rosemont, all of Pa.

[73] Assignees: Trustees of the University of Penna., Philadelphia, Pa.; Merck Company, Rahway, N.J.

[21] Appl. No.: 269,583

[22] Filed: Nov. 10, 1988

[51] Int. Cl.$^5$ .................. A61K 37/00; C07K 1/00
[52] U.S. Cl. .................... 514/13; 514/822; 514/929; 530/326
[58] Field of Search ............. 514/12, 13, 822, 929; 530/326, 806, 380, 381, 382, 383, 384

[56] References Cited

U.S. PATENT DOCUMENTS

| | | |
|---|---|---|
| 4,244,946 | 1/1981 | Rivier et al. |
| 4,305,872 | 12/1981 | Johnston et al. |
| 4,316,891 | 2/1982 | Guillemin et al. |
| 4,578,079 | 3/1986 | Ruslahti et al. |
| 4,614,517 | 9/1986 | Ruoslahti et al. |
| 4,683,291 | 7/1987 | Zimmerman et al. |
| 4,769,239 | 9/1988 | Ellis et al. ................ 424/89 |

FOREIGN PATENT DOCUMENTS 51-08271 of 1976 Japan.

OTHER PUBLICATIONS

Auffray et al. Human Immun. vol. 15 381–390 (1986).
Rao et al., Biochem. vol. 26 3556–3564 (1987).
Titani et al., Biochem. vol. 25, 3171–3184 (1986).
Shattil et al., J. Biol. Chem. vol. 260 No. 20, (1985) 11107–11114.
Geliebter, Focus vol. 9: 5–8 (1987).
Tachibana et al., JP 51082710 (1976-Abstract).
Rudinger, Peptide Hormones (Jun. 1976) 1–6.
Chen et al., Virology vol. 155 106–119 (1986).
Bodansky, M., ed., Principles of Peptide Synthesis, Springer-Verlag, (1984).
Gennaro, A. R., ed., Remington's Pharmaceutical Sciences, (Mack Publishing Co., Easton, Pa. 1985).
Gross and Mienhofer, eds., The Peptides, vol. 3, pp. 3–88 (Academic Press, NY, 1981).
Kabat, E. A., et al., Sequences of Proteins of Immunologic Interest, (US, DHHS, PHS, NIH 1987).
Maniatis et al., Molecular Cloning, A Laboratory Manual, (Cold Spring Harbour 1982).
Segal, Enzyme Kinetics, 465–504 (Wiley-Interscience, NY 1975).
Ross and Aviv et al., "In Vitro Synthesis of DNA Complementary to Purified Rabbit Globin mRNA 38 ", Proc. Natl. Acad. Sci., 69: 264–268 (1972).
Rouslahti et al., "New Perspectives in Cell Adhesion: RGD and Integrins 38 ", Science, 238: 491–497 (1987).
Shlomchik et al., "Variable Region Sequencesof Murine IgM Anti-IgG Monoclonal Autoantibodies", J. Exp. Med., 164: 407–427 (1986).
Shattil et al., "Detection of Activated Platelets in Whole Blood Using Activation-Dependent Monoclonal Antibodies and Flow Cytometry 38 ", Blood, 70: 307–315 (1987).
Shattil et al., "Expression fo Fibrinogen Receptors During Activation and Subsequent Desenitization of Human Platelets by Epinephrine", Blood, 68: 1224–1231 (1986).
Tam et al., "$S_N2$ Deprotection of Synthetic Peptides with a Low Concentration of HF in Dimethyl Sulfide: Evidence and Application in Peptide Synthesis", J. Am. Chem. Soc., 105: 6442–6455 (1983).
Vale et al., "Characterization of a 41-Residue Ovine Hypothalamic Peptide That Stimulates Secretion of (List continued on next page.)

Primary Examiner—Merrell C. Cashion, Jr.
Assistant Examiner—B. Celsa
Attorney, Agent, or Firm—Woodcock Washburn Kurtz Mackiewicz & Norris

[57] ABSTRACT

Peptides comprising the tripeptide sequence of arginine-tyrosine-aspartic acid, linked from amino- to carboxy-terminus, are inhibitors of fibrinogen binding, platelet aggregation, glycoprotein IIb-IIIa binding and related aberrant and normal physiological conditions.

6 Claims, 8 Drawing Sheets

PAC1-κ Variable Region

```
                                    30                                          60
GAT GTT TTG ATG ACC CAA ACT CCA CTC TCC CTG CCT GTC AGT CTT GGA GAT CAA GCC TCC
                  10                                                            20
Asp Val Leu Met Thr Gln Thr Pro Leu Ser Leu Pro Val Ser Leu Gly Asp Gln Ala Ser
                               90                                             120
ATC TCT TGC AGA TCT AGT CAG AGC ATT GTA CAT AGT AAT GGA AAC ACC TAT TTA GAA TGG
              27    A   B   C   D   E   28 CDR1                                35
Ile Ser Cys |Arg Ser Ser Gln Ser Ile Val His Ser Asn Gly Asn Thr Tyr Leu Glu| Trp
                                       150                                    180
TAC CTG CAG AAA CCA GGC CAG TCT CCA AAG CTC CTG ATC TAC AAA GTT TCC AAC CGA TTT
                                45                         CDR2               55
Tyr Leu Gln Lys Pro Gly Gln Ser Pro Lys Leu Leu Ile Try |Lys Val Ser Asn Arg Phe|
                                      210                                     240
TCT GGG GTC CCA GAC AGG TTC ACT GGC AGT GGA TCA GGT ACA GAT TTC ACA CTC AAG ATC
                                 65                                            75
|Ser| Gly Val Pro Asp Arg Phe Thr Gly Ser Gly Ser Gly Thr Asp Phe Thr Leu Lys Ile
                                     270                                    V 300
AGC AGA GTG GAG GCT GAG GAT CTG GGA GTT TAT TAC TGC TGG CAA GGT TCA CAT GTT CCG
                                85                                    CDR3   95
Ser Arg Val Glu Ala Glu Asp Leu Gly Val Tyr Tyr Cys |Trp Gln Gly Ser His Val Pro|
|J2                                           336
TAC ACG TTC GGA GGG GGG ACC AAG CTG GAA ATA AAA
                                          107
|Tyr Thr| Phe Gly Gly Gly Thr Lys Leu Glu Ile Lys
```

OTHER PUBLICATIONS

Corticotropin and β-Endorphin", *Science*, 213: 1394–1397.

Kohler et al., "Continuous Cultures of Fused Cells Secreting Antibody of Predefined Specificity", *Nature*, 256: 495–497 (1975).

McEver et al., "A Monoclonal Antibody to a Membrane Glycoprotein Binds Only to Activated Platelets", *J. Biol. Chem.*, 259: 9799–9804 (1984).

Marguerie et al., "Human Platelets Possess an Inducible and Saturable Receptor Specific for Fibrinogen", *J. Biol. Chem.*, 254: 5357–5363 (1979).

Marki et al., "Total Solid-Phase Synthesis of Porcine Gut Gastrin Releasing Peptide (GRP), a Mammalian Bombesin", *J. Am. Chem. Soc.*, 103: 3178–3185 (1981).

Merrifield, "Solid Phase Peptide Synthesis. I. The Synthesis of a Tetrapeptide", *J. Am. Chem. Soc.*, 85: 2149–2154 (1963).

Phillis et al., "The Platelet Membrane Glycoprotein IIb-IIIa Complex", *Blood*, 71: 831–843 (1988).

Pytela et al., "Platelet Membrane Glycoprotein IIb-/IIIa:Member of a Family of Arg-Gly-Asp-Specific Adhesion Receptors", *Science*, 231: 1559–1562 (1986).

Riechmann et al., "Reshaping Human Antibodies for Therapy", *Nature*, 332: 323–327 (1988).

River et al., "Peptide and Amino Acid Analysis By RP-HPLC", *Peptides: The structure and Biological Function*, 125–128 (1979).

Haverstick et al., "Inhibition of Platelet Adhesion to Fibronectin, Fibrinogen, and von Willebrand Factor Substrates by a Synthetic Tetrapeptide Derived from the Cell Binding Domain of Fibronectin", *Blood*, 66:946–952 (1985).

Houghten, "General Method for the Rapid Solid-phase Synthesis of Large Numbers of Peptides: Specificity of antigen-antibody interaction at the level of individual amino acids", *Proc. Natl. Acad. Sci. U.S.A.*, 82: 5131–5135 (1985).

Humphries et al., "Identification of an Alternatively Spliced Site in Human Plasma Fibronectin That Mediates Cell Type-specific Adhesion", *J. Cell Biol.*, 103: 2637–2647 (1986).

Hynes, "Integrins: A Family of Cell Surface Receptors", *Cell*, 48: 549–554 (1987).

Kloczewiak et al., "Platelet Receptor Recognition Site on Human Fibrinogen. Synthesis and Structure-Function Relationship of Peptides Corresponding to the Carboxy-Terminal Segment of the γ Chain", *Biochemistry*, 23: 1767–1774 (1984).

Kloczewiak et al., "Recognition Site for the Platelet Receptor is Present on the 15-Residue Carboxy-Terminal Fragment of the }Chain of Human Fibrinogen and is Not Involved in the Fibrin Polymerization Reaction," *Thrombosis Res.*, 29: 249–255 (1983).

Abrams et al., "Platelet Activation and Fragmentation During Cardiopulmonary Bypass Can be Detected by Flow Cytometry of Whole Blood", *Blood*, 70: 335a (1987).

Bennett et al., "Interaction of Fibrinogen with Its Platelet Receptor", *J. Biol. Chem.*, 263: 1–6 (1988).

Bennett et al., "Exposure of Platelet Fibrinogen Receptors by ADP and Epinephrine", *J. Clin. Invest.*, 64: 1393–1401 (1979).

Bennett et al., "Inhibition of Fibrinogen Binding to Stimulated Human Platelets by a Monoclonal Antibody", *Proc. Natl. Acad. Sci. U.S.A.*, 80: 2417–2421 (1983).

Chirgwin et al., "Isolation of Biologically Active Ribonucleic Acid from Sources Enriched in Ribonucleases", *Biochemistry*, 18: 5294–5299 (1979).

Gartner et al., "The Tetrapeptide Analogue of the Cell Attachment Site of Fibronectin Inhibits Platelet Aggregation and Fibrinogen Binding to Activated Platelets", *J. Biol. Chem.*, 260: 11891–11894 (1985).

Ginsberg et al., "Inhibition of Fibronectin Binding to Platelets by Proteolytic Fragments and Synthetic Peptides Which Support Fibroblast Adhesion", *J. Biol. Chem.*, 260:3931–3936 (1985).

Bennett et al., "Interaction of Fibrinogen with Its Platelet Receptor", *J. Biol. Chem.*, vol. 263, No. 26, pp. 12948–12953 (1988).

Goetinck et al., "The Tandemly Repeated Sequences of Cartilage Link Protein Contain the Sites for Interaction with Hyaluronic Acid", *J. Cell Biol.*, vol. 105, pp. 2403–2408 (1987).

PAC1-κ Variable Region

```
                            30                                60
GAT GTT TTG ATG ACC CAA ACT CCA CTC TCC CTG CCT GTC AGT CTT GGA GAT CAA GCC TCC
Asp Val Leu Met Thr Gln Thr Pro Leu Ser Leu Pro Val Ser Leu Gly Asp Gln Ala Ser
                    10                                90                      120
ATC TCT TGC AGA TCT AGT CAG AGC ATT GTA CAT AGT AAT GGA AAC ACC TAT TTA GAA TGG
Ile Ser Cys Arg Ser Ser Gln Ser Ile Val His Ser Asn Gly Asn Thr Tyr Leu Glu Trp
           27  A   B   C   D   E  28                              35
                  CDR1                                                       180
           150
TAC CTG CAG AAA CCA GGC CAG TCT CCA AAG CTC CTG ATC TAC AAA GTT TCC AAC CGA TTT
Tyr Leu Gln Lys Pro Gly Gln Ser Pro Lys Leu Leu Ile Try Lys Val Ser Asn Arg Phe
                                45                               CDR2       55
                                           210                              240
TCT GGG GTC CCA GAC AGG TTC ACT GGC AGT GGA TCA GGT ACA GAT TTC ACA CTC AAG ATC
Ser Gly Val Pro Asp Arg Phe Thr Gly Ser Gly Thr Asp Phe Thr Leu Lys Ile
 J2                                     65                               75
                                           270                              300
AGC AGA GTG GAG GCT GAG GAT CTG GGA GTT TAT TAC TGC TGG CAA GGT TCA CAT GTT CCG
Ser Arg Val Glu Ala Glu Asp Leu Gly Val Tyr Tyr Cys Trp Gln Gly Ser His Val Pro
                                   85                    CDR3            95
                                           336
TAC ACG TTC GGA GGG GGG ACC AAG CTG GAA ATA AAA
Tyr Thr Phe Gly Gly Gly Thr Lys Leu Glu Ile Lys
                                       107
```

Fig. 1

PAC1-μ Variable Region

```
CAG GTG CAG CTG AAG CAG TCA GGA CCT GGC CTA GTG CAG CCC TCA CAG AGC CTG TCC ATC     60
Gln Val Gln Leu Lys Gln Ser Gly Pro Gly Leu Val Gln Pro Ser Gln Ser Leu Ser Ile     20
             10                          20
ACC TGC ACA GTC TCT GGT TTC TCA TTA ACT AGC TAT GGT GTA CAC TGG GTT CGC CTG TCT    120
Thr Cys Thr Val Ser Gly Phe Ser Leu Thr Ser Tyr Gly Val His Trp Val Arg Leu Ser     40
             30                          CDR1        40
CCA GGA AAG GGT CTG GAG TGG CTG GGA GTG ATA TGG AGT GGT GGA AGC ACA GAC TAT AAT    180
Pro Gly Lys Gly Leu Glu Trp Leu Gly Val Ile Trp Ser Gly Gly Ser Thr Asp Tyr Asn     60
             50                         CDR2         60
GCA GCT TTC ATA TCC AGA CTG AGC AGC CTG AAG TCC AAG AGC CAA GTT TTC TTT            240
Ala Ala Phe Ile Ser Arg Leu Ser Ser Leu Lys Ser Lys Ser Gln Val Phe Phe             80
             70                          V|D
AAA ATG AAC AGT CTG CAA GCT AAT GAC ACA GGG ATA TAT TAC TGT GCC AGA AGA AGC CCC    300
Lys Met Asn Ser Leu Gln Ala Asn Asp Thr Gly Ile Tyr Tyr Cys Ala Arg Arg Ser Pro     97
    82           A   B   C   83              330D|J4
                                                            CDR3
TCC TAC TAT AGG TAT GAC GCG GGG CCT TAT GCT ATG GAC TAC TGG GGT CAA GGA            360
Ser Tyr Tyr Arg Tyr Asp Ala Gly Pro Tyr Ala Met Asp Tyr Trp Gly Gln Gly            106
CDR3 100  A   B   C   D   E   F   G   H   I   J   K 101
ACC TCA GTC ACC GTC TCC TCA                                                        378
Thr Ser Val Thr Val Ser Ser                                                        113
```

INHIBITORS OF PLATELET BINDING

BACKGROUND OF THE INVENTION

Many adhesive proteins, including fibrinogen, fibronectin, von Willebrand factor, and vitronectin, contain an amino acid sequence that functions as a recognition site for adhesion receptors. The amino acid sequences within these proteins are recognized by structurally-related receptors on a variety of mammalian cells that have been termed integrins or cytoadhesions. Hynes, *Cell,* 48, 549-554 (1987); Ruoslahti et al., *Science,* 238, 491-497 (1987).

One well-characterized member of the integrin family is the blood platelet membrane glycoprotein IIb-IIIa complex (GP IIb-IIIa). Phillips et al., *Blood,* 71, 831-843 (1988). Upon platelet activation, GP IIb-IIIa becomes competent to bind fibrinogen, a process required for platelet aggregation. Bennett et al., *J. Clin. Invest.,* 64, 1393-1400 (1979); Marguerie et al., *J. Biol. Chem.,* 254, 5357-5363 (1979). Based on studies with synthetic peptides, the Arg-Gly-Asp-Ser sequence at positions 572-575 of the fibrinogen Aα chain appears to play a major role in the interaction of this protein with GP IIb-IIIa, although other regions in fibrinogen may be involved as well. Gartner et al., *J. Biol. Chem.,* 260, 11891-11894 (1985); Ginsberg et al., *J. Biol. Chem.,* 260, 3931-3936 (1985); Haverstick et al., Blood, 66, 946-952 (1985); Pytela et al., *Science,* 231, 1159-1162 (1986); Kloczewiak et al., *Thrombosis Res.,* 29, 249-255 (1983); Kloczewiak et al., *Biochemistry,.* 23, 1767-1774 (1984). However, the precise details of the molecular interaction between fibrinogen and GP IIb-IIIa are, at present, unknown. The tripeptide sequence Arg-Gly-Asp has also been identified in the adhesive proteins fibronectin, von Willebrand factor and vitronectin. Hynes, *Cell,* 48, 549-554 (1987); Ruoslahti et al., *Science,* 238, 491-497 (1987). A similar region of fibronectin containing the sequence Arg-Glu-Asp-Val has been implicated in the binding of this protein to melanoma cells. Humphries et al., *J. Cell Biol.,* 103, 2637-2647 (1986). Moreover, von Willebrand factor, which can bind to GP IIb-IIIa on activated platelets, contains, in its long (significantly greater than 50 residue) amino acid sequence, an Arg-Tyr-Asp-Ala, in addition to an Arg-Gly-Asp-Ser, sequence. Titani et al., *Biochemistry,* 25, 3171-3184 (1986). Furthermore, the sequences Arg-Phe-Asp-Ser and Arg-Tyr-Asp-Ser are found within the long chain peptides that comprise the major histocompatibility antigens, peptides which have a length greatly in excess of 50 amino acid residues. Auffray et al., *Human Immunol.,* 15, 381-390 (1986).

Numerous applications have been found for peptides containing the amino acid sequence Arg-Gly-Asp. The binding of fibrinogen to blood platelets, for example, has been found to be inhibited by Arg-Gly-Asp-containing peptides. In addition, PAC1, an IgM-κ murine monoclonal antibody that, like fibrinogen, appears to bind to GP IIb-IIIa on activated platelets, is similarly inhibited by such peptides. The inhibition of fibrinogen and PAC1 occurs at an apparent Ki of about 10-20 μM when the tetrapeptide Arg-Gly-Asp-Ser is employed. Shattil et al., *J. Biol. Chem.,* 260, 11107-11114 (1985); Bennett et al., *J. Biol. Chem.,* (1988); Shattil et al., *Blood,* 68, 1224-1231 (1986). Moreover, U.S. Pat. No. 4,683,291 discloses the usefulness of peptides containing the Arg-Gly-Asp sequence in inhibiting cellular adhesion in general, and platelet to platelet binding specifically. Such peptides are also reported as useful in retarding the formation of blood clots.

Additional and/or better peptides which meet the important ends of inhibiting fibrinogen to platelet binding, platelet to platelet binding and/or blood clot formation are needed. The present invention is directed to these and other important needs.

SUMMARY OF THE INVENTION

The present invention provides compounds of the general Formula I

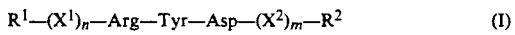

$$R^1-(X^1)_n-Arg-Tyr-Asp-(X^2)_m-R^2 \qquad (I)$$

and physiologically acceptable salts thereof, wherein:

$X^1$ and $X^2$, independently, are 1 to about 50 amino acid residues, provided that the total number of amino acid residues in $X^1$ and $X^2$, taken together, is less than or equal to about 50;

m and n, independently, are 0 or 1;

$R^1$ is $R^2$ is a protected or unprotected terminal carboxy group.

Also included in the subject invention are compounds of the general Formula II

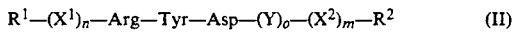

$$R^1-(X^1)_n-Arg-Tyr-Asp-(Y)_o-(X^2)_m-R^2 \qquad (II)$$

and physiologically acceptable salts thereof, wherein:

$X^1$ and $X^2$, independently, are 1 or more amino acid residues;

Y is 1 or more amino acid residues, provided that Y does not include a Ser or Ala residue;

m, n and o, independently, are 0 or 1, provided that when m is 1, o must be 1;

$R^1$ is a protected or unprotected terminal amino group; and $R^2$ is a protected or unprotected terminal carboxy group; and wherein said compound inhibits fibrinogen binding, platelet aggregation, glycoprotein IIb-IIIa binding, thrombosis and/or cancer metastasis.

The invention further provides compositions comprising one or more of the foregoing compounds, and methods of using such compounds or compositions in inhibiting fibrinogen binding, platelet aggregation, and/or glycoprotein IIb-IIa binding, The subject compounds or compositions are also effective in the treatment of certain physiological conditions, such as thrombosis and/or cancer metastasis, and the present invention is further directed to these uses.

Also included within the ambit of the present invention are monoclonal and polyclonal antibodies directed to the subject compounds and nucleic acid fragments comprising nucleotide sequences which encode the subject compounds.

Finally, the present invention comprehends a peptide comprising an amino acid sequence corresponding to the amino acid sequence of the variable region of the μ heavy chain of monoclonal antibody PAC1, as well as antibodies incorporating that sequence. The present invention further includes a peptide comprising an amino acid sequence corresponding to the amino acid sequence of the variable region of the μ heavy chain of monoclonal antibody PAC1, and an amino acid sequence corresponding to the amino acid sequence of the variable region of the κ light chain of monoclonal antibody PAC1, as well as antibodies incorporating that sequence. Most specifically, the invention is directed to the monoclonal antibody PAC1.

BRIEF DESCRIPTION OF THE DRAWINGS

FIG. 1 shows the nucleotide sequence of the variable region of the κ light chain of a PAC1 hybridoma cell, with nucleotide numbering shown above. The site of the V to J region junction is indicated. The predicted amino acid sequence, along with the amino acid numbers appear on the next two lines below. The amino acids are numbered according to convention. Kabat E. A., Wu, T. T., Reid-Miller, M., Perry, H. M., Gottesman, K. S., *Sequences of Proteins of Immunologic Interest* (US DHHS, PHS, NIH 1987). The complimentary determining regions (CDRs) are shown in boxes.

FIG. 2 shows the nucleotide sequence of the variable region of the μ heavy chain of a PAC1 hybridoma cell with nucleotide numbering shown above. The site of the V to J region junction is indicated. The predicted amino acid sequence, along with the amino acid numbers appear on the next two lines below. The amino acids are numbered according to convention. Kabat E. A., Wu, T. T., Reid-Miller, M., Perry, H. M., Gottesman, K. S., *Sequences of Proteins of Immunologic Interest* (US DHHS, PHS, NIH 1987). The complimentary determining regions (CDRs) are shown in boxes. CRD3 is comprised of the amino acid sequence Arg-Ser-Pro-Ser-Tyr-Tyr-Arg-Tyr-Asp-Gly-Ala-Gly-Pro-Tyr-Tyr-Ala-Met-Asp-Tyr.

In FIG. 2A, the data points without error bars represent the mean of two experiments.

DETAILED DESCRIPTION OF THE INVENTION

Figure 3A:
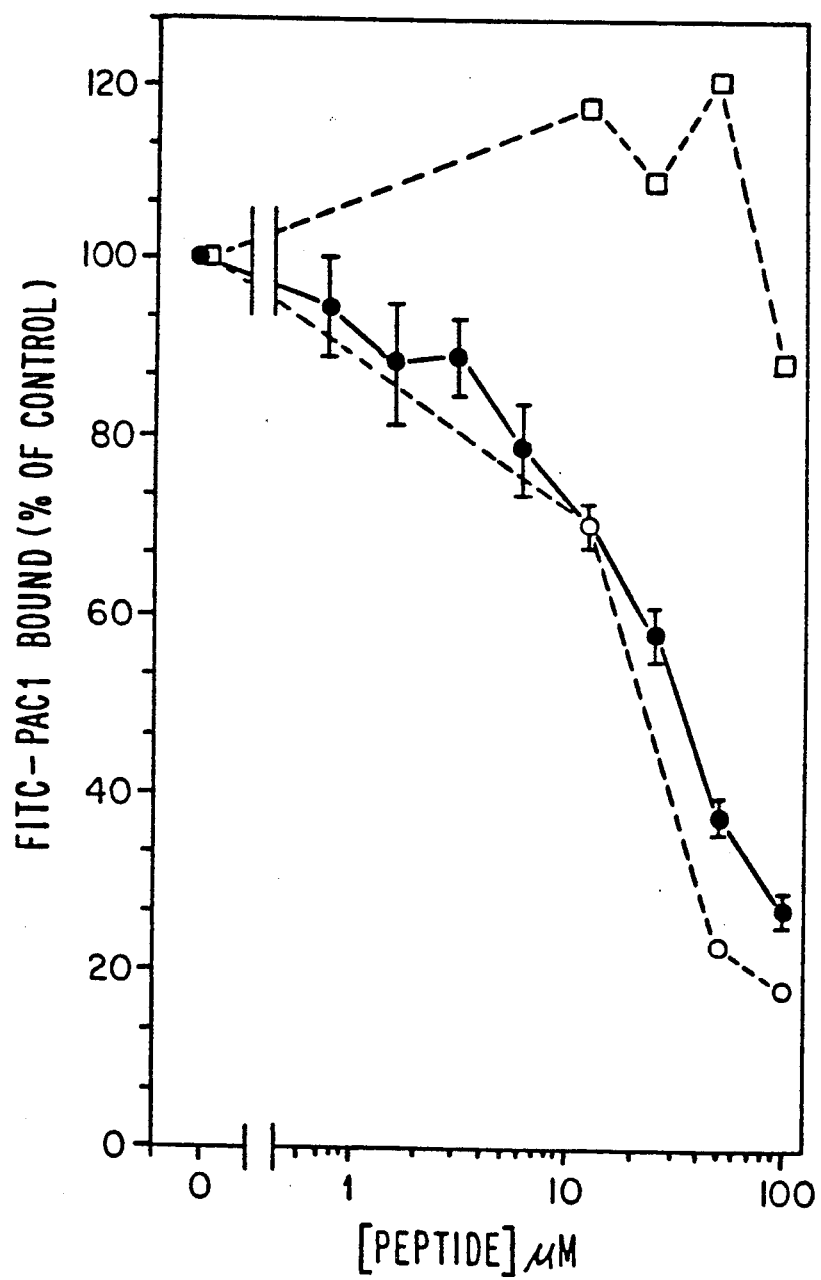
FIG. 3 shows the effect of a 21 amino acid peptide derived from the variable region of the PAC1 μ heavy chain (hereinafter referred to as "the Arg-Tyr-Asp-21mer peptide") on the binding of PAC1 and fibrinogen to activated human blood platelets. The Arg-Tyr-Asp-21mer has the sequence Ala-Arg-Arg-Ser-Pro-Ser-Tyr-Tyr-Arg-Tyr-Asp-Gly-Ala-Gly-Pro-Tyr-Tyr-Ala-Met-Asp-Tyr. Gel-filtered platelets were incubated for 15 min with ADP (10 μM), and epinephrine (10 μM), in the presence of various peptides and either FITC-PAC1 (FIG. 3A) or FITC-9F9 (FIG. 3B) and fibrinogen (50 μg/ml). The specific peptides tested were Arg-Tyr-Asp-21mer (filled circles), Arg-Gly-Asp-Ser (unfilled circles) and an unrelated-28mer (control; unfilled squares). Binding was determined by flow cytometry. Antibody binding is expressed as the percent of binding observed in the absence of added peptide. Error bars represent the mean ±SEM of 5 separate experiments.

The present invention involves the discovery of novel and very active compounds that contain the tripeptide sequence of arginine-tyrosine-aspartic acid, linked from amino- to carboxy-terminus. The subject invention derives from the surprising finding that the arginine-tyrosine-aspartic acid sequence is present in one of the heavy chain hyper-variable regions of PAC1 murine monoclonal immunoglobulin, and in that position is a potential mediator in the binding of this monoclonal antibody to the blood platelet membrane fibrinogen receptor, glycoprotein IIb-IIIa.

More specifically, the present invention encompasses peptide compounds of the general Formula I

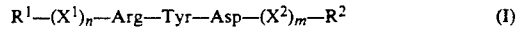

$$R^1—(X^1)_n—Arg—Tyr—Asp—(X^2)_m—R^2 \quad (I)$$

and physiologically acceptable salts thereof. The present invention further encompasses peptide compounds of the general Formula II

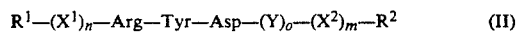

$$R^1—(X^1)_n—Arg—Tyr—Asp—(Y)_o—(X^2)_m—R^2 \quad (II)$$

and physiologically acceptable salts thereof. These compounds are characterized by their inhibitory potency, namely their ability to retard or prevent the following: the binding of the adhesive protein fibrinogen to blood platelets (referred to herein as inhibiting "fibrinogen binding"); the binding blood platelets to themselves (referred to herein as inhibiting "platelet aggregation"); and/or the binding of compounds or substances, particularly proteins, to the glycoprotein IIb-IIIa complex found in blood platelet membranes (referred to herein inhibiting "glycoprotein IIb-IIIa binding"). The subject compounds are also useful in retarding o preventing the formation of blood clots or thrombi (referred to herein as inhibiting "thrombosis") and/or the spread of cancer cells throughout the body (referred to herein as inhibiting "cancer metastasis"). The selectivity of these compounds in carrying out the foregoing related activities makes them particularly useful as therapeutic and/or diagnostic agents.

As used throughout this specification, amino acid residues are denoted by the following abbreviations:

| Alanine | = | Ala |
| Arginine | = | Arg |
| Asparagine | = | Asn |
| Aspartic acid | = | Asp |
| Cysteine | = | Cys |
| Glutamic acid | = | Glu |
| Glutamine | = | Gln |
| Glycine | = | Gly |
| Histidine | = | His |
| Isoleucine | = | Ile |
| Leucine | = | Leu |
| Lysine | = | Lys |
| Methionine | = | Met |
| Phenylalanine | = | Phe |
| Proline | = | Pro |
| Serine | = | Ser |
| Threonine | = | Thr |
| Tryptophan | = | Trp |
| Tyrosine | = | Tyr |
| Valine | = | Val |

For maximal activity, the amino acid residues comprising the key tripeptide region, Arg-Tyr-Asp, of the subject invention must be in the L-configuration. The remaining amino acid residues of the subject invention can be present in either the D- or the L-configuration.

As previously noted, in the above Formula I, $X^1$ and $X^2$, and in the above Formula II, $X^1$, $X^2$ and Y, may each independently comprise one or more amino acid residues. The $X^1$, $X^2$ and/or Y amino acid residues, as the case may be, may be linked among themselves, or with each other, in branched, cyclical or straight chain form, although straight chain linkages are preferred. As one skilled in the art would recognize, branched or cyclical chains may be produced by the formation of a peptide bond with amino acid side groups that contain amino or carboxyl moieties. Amino acids containing such side groups include, for example, glutamic acid (carboxyl group), aspartic acid (carboxyl group) and lysine (amide group). Branched or cyclical chains may also be produced through the formation of a covalent disulfide bond between amino acid residues having sulfur-containing side groups, such as cysteine.

In Formula I, as noted above, m and n may be, independently, 0 or 1—that is, m and n may both be 0 or may both be 1, or m may be 0 when n is 1, or m may be 1 when n is 0. Where both m and n are 0, the subject invention comprises a tripeptide of the sequence Arg-Tyr-Asp, linked, in order, from amino- to carboxy-terminus. Similarly, in Formula II, when each of m, n and o is 0, the subject invention is also directed to the tripeptide Arg-Tyr-Asp.

The $R^1$ substituent of Formulas I or II may be either an unprotected or protected terminal amino group (amino-terminus). Similarly, $R^2$ may be either an unprotected or protected terminal carboxy group (carboxy-terminus).

As used herein, "protected" terminal amino group, refers to a terminal amino group coupled with any of various amino-terminal protecting groups traditionally employed in peptide synthesis. Examples of suitable groups include acyl protecting groups, for example, formyl, acetyl, benzoyl, trifluoroacetyl, succinyl and methoxysuccinyl; aromatic urethane protecting groups, for example, benzyloxycarbonyl; and aliphatic urethane protecting groups, for example, tert-butoxycarbonyl or adamantyloxycarbonyl. Gross and Mienhofer, eds., *The Peptides.* Vol. 3, pp. 3–88 (Academic Press, New York, 1981), disclose numerous suitable terminal amino protecting groups.

The following represent preferred amino terminal protecting groups:

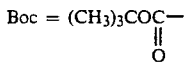

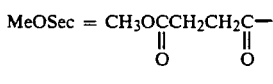

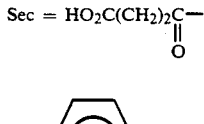

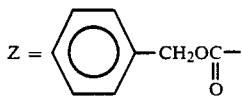

The amino acid residues of the $X^1$, $X^2$ and Y substituents having side-chain amino groups, for example, Lys or Arg, can optionally comprise suitable amino-terminal protecting groups attached to the side chains.

As used herein, "protected" terminal carboxyl group, refers to a terminal carboxyl group coupled with any of various carboxy-terminal protecting groups. As will be readily apparent to one skilled in the art, suitable groups include tert-butyl, benzyl or other acceptable groups linked to the terminal carboxyl group through an ester or ether bond. Amino acid residues of the $X^1$, $X^2$ and Y substituents having acidic or hydroxy side chains can be similarly protected.

The present invention also contemplates physiologically acceptable salts of Formulas I and II. These salts include acid addition salts, for example, salts of hydrochloric acid, hydrobromic acid, acetic acid, trifluoroacetic acid, citric acid, succinic acid, benzene sulfonic acid or other suitable acid addition salts.

Preferable classes of compounds within the scope of Formula I include:

Compounds wherein
  m is 0; and
  n is 0.
Compounds wherein $X^1$ and $X^2$ are in straight chain forms.
Compounds wherein the total number of amino acid residues in $X^1$ and $X^2$, taken together, is less than about 40.
Compounds wherein the total number of amino acid residues in $X^1$ and $X^2$, taken together, is less than about 25.
Compounds wherein the total number of amino acid residues in $X^1$ and $X^2$, taken together, is less than about 10.
Compounds wherein
  $X^1$ is Ala-Arg-Arg-Ser-Pro-Ser-Tyr-Tyr;
  $X^2$ is Gly-Ala-Gly-Pro-Tyr-Tyr-Ala-Met-Asp-Tyr;
  m is 1; and
  n is 1.
Compounds wherein $X^1$ is Ala-Arg-Arg-Ser-Pro-Ser-Tyr-Tyr;
$X^2$ is Gly-Ala-Gly-Pro-Tyr-Tyr-Ala-Met-Asp-Tyr;
m is 1; and
n is 1.
Compounds wherein
$X^1$ is Gln-Val-Gln-Leu-Lys-Gln-Ser-Gly-Pro Gly-Leu-Val-Gln-Pro-Ser-Gln-Ser-Leu-Ser-Ile-Thr-Cys-Thr-Val-Ser-Gly-Phe-Ser-Leu-Thr-Ser-Tyr-Gly-Val-His-Trp-Val-Arg-Leu-Ser-Pro-Gly-Lys-Gly-Leu-Glu-Trp-Leu-Gly-Val-Ile-Trp-Ser-Gly-Gly-Ser-Thr-Asp-Tyr-Asn-Ala-Ala-Phe-Ile-Ser-Arg-Leu-Ser-Ile-Ser-Lys-Asp-Asn-Ser-Lys-Ser-Gln-Val-Phe-Phe-Lys- Met-Asn-Ser-Leu-Gln-Ala-Asn-Asp-Thr-Gly-Ile-Tyr-Tyr-Cys-Ala-Arg-Arg-Ser-Pro-Ser-Tyr-Tyr;
$X^2$ is Gly-Ala-Gly-Pro-Tyr-Tyr-Ala-Met-Asp Tyr-Trp-Gly-Gln-Gly-Thr-Ser-Val-Thr-Val-Ser-Ser;
m is 1; and
n is 1.
Compounds wherein
$X^1$ is Gln-Val-Gln-Leu-Lys-Gln-Ser-Gly-Pro Gly-Leu-Val-Gln-Pro-Ser-Gln-Ser-Leu-Ser-Ile-Thr-Cys-Thr-Val-Ser-Gly-Phe-Ser-Leu-Thr-Ser-Tyr-Gly-Val-His-Trp-Val-Arg-Leu-Ser-Pro-Gly-Lys-Gly-Leu-Glu-Trp-Leu-Gly-Val-Ile-Trp-Ser-Gly-Gly-Ser-Thr-Asp-Tyr-Asn-Ala-Ala-Phe-Ile-Ser-Arg-Leu-Ser-Ile-Ser-Lys-Asp-Asn-Ser-Lys-Ser-Gln-Val-Phe-Phe-Lys-Met-Asn-Ser-Leu-Gln-Ala-Asn-Asp-Thr-Gly-Ile-Tyr-Tyr-Cys-Ala-Arg-Arg-Ser-Pro-Ser-Tyr-Tyr;
$X^2$ is Gly-Ala-Gly-Pro-Tyr-Tyr-Ala-Met-Asp Tyr-Trp-Gly-Gln-Gly-Thr-Ser-Val-Thr-Val-Ser-Ser;
m is 1; and
n is 1.
Compounds wherein
$R^1$ is an unprotected terminal amino group; and
$R^2$ is an unprotected terminal carboxy group.
Preferable classes of compounds within the scope of Formula II include:
Compounds wherein
m is 0;
n is 0; and
o is 0.
Compounds wherein $X^1$, $X^2$ and Y are in straight chain forms.
Compounds wherein the total number of amino acid residues in $X^1$, $X^2$ and Y, taken together, is less than about 250.
Compounds wherein the total number of amino acid residues in $X^1$, $X^2$ and Y, taken together, is less than about 200.
Compounds wherein the total number of amino acid residues in $X^1$, $X^2$ and Y, taken together, is less than about 100.
Compounds wherein the total number of amino acid residues in $X^1$, $X^2$ and Y, taken together, is less than about 50.
Compounds wherein the total number of amino acid residues in $X^1$, $X^2$ and Y, taken together, is less than about 40.
Compounds wherein the total number of amino acid residues in $X^1$, $X^2$ and Y, taken together, is less than about 25.
Compounds wherein the total number of amino acid residues in $X^1$, $X^2$ and Y, taken together, is less than about 10.
Compounds wherein
$X^1$ is Ala-Arg-Arg-Ser-Pro-Ser-Tyr-Tyr;
$X^2$ is Gly-Ala-Gly-Pro-Tyr-Tyr-Ala-Met-Asp-Tyr;
m is 1;
n is 1; and
o is 0.
Compounds wherein
$X^1$ is Ala-Arg-Arg-Ser-Pro-Ser-Tyr-Tyr;
$X^2$ is Gly-Ala-Gly-Pro-Tyr-Tyr-Ala-Met-Asp-Tyr;
m is 1;
n is 1; and
o is 0.
Compounds wherein
$X^1$ is Gln-Val-Gln-Leu-Lys-Gln-Ser-Gly-Pro Gly-Leu-Val-Gln-Pro-Ser-Gln-Ser-Leu-Ser-Ile-Thr-Cys-Thr-Val-Ser-Gly-Phe-Ser-Leu-Thr-Ser-Tyr-Gly-Val-His-Trp-Val-Arg-Leu-Ser-Pro-Gly-Lys-Gly-Leu-Glu-Trp-Leu-Gly-Val-Ile-Trp-Ser-Gly-Gly-Ser-Thr-Asp-Tyr-Asn-Ala-Ala-Phe-Ile-Ser-Arg-Leu-Ser-Ile-Met-Asn-Ser-Leu-Gln-Ala-Asn-Asp-Thr-Gly-Ile-Tyr-Tyr-Cys-Ala-Arg-Arg-Ser-Pro-Ser-Tyr-Tyr;
$X^2$ is Gly-Ala-Gly-Pro-Tyr-Tyr-Ala-Met-Asp Tyr-Trp-Gly-Gln-Gly-Thr-Ser-Val-Thr-Val-Ser-Ser;
m is 1;
n is 1; and
o is 0.
Compounds wherein
$X^1$ is Gln-Val-Gln-Leu-Lys-Gln-Ser-Gly-Pro Gly-Leu-Val-Gln-Pro-Ser-Gln-Ser-Leu-Ser-Ile-Thr-Cys-Thr-Val-Ser-Gly-Phe-Ser-Leu-Thr-Ser-Tyr-Gly-Val-His-Trp-Val-Arg-Leu-Ser-Pro-Gly-Lys-Gly-Leu-Glu-Trp-Leu-Gly-Val-Ile-Trp-Ser-Gly-Gly-Ser-Thr-Asp-Tyr-Asn-Ala-Ala-Phe-Ile-Ser-Arg-Leu-Ser-Ile-Ser-Lys-Asp-Asn-Ser-Lys-Ser-Gln-Val-Phe-Phe-Lys-Met-Asn-Ser-Leu-Gln-Ala-Asn-Asp-Thr-Gly-Ile-Tyr-Tyr-Cys-Ala-Arg-Arg-Ser-Pro-Ser-Tyr-Tyr;
$X^2$ is Gly-Ala-Gly-Pro-Tyr-Tyr-Ala-Met-Asp Tyr-Trp-Gly-Gln-Gly-Thr-Ser-Val-Thr-Val-Ser-Ser;
m is 1;
n is 1; and
o is 0.
Compounds wherein
$R^1$ is an unprotected terminal amino group; and
$R^2$ is an unprotected terminal carboxy group.
Obvious equivalents of the foregoing compounds include compounds comprising less common or modified amino acids, for example, hydroxyproline, hydroxylysine, cystine, thyroxine, norleucine, pyroglutamic acid or other derivatives capable of incorporation into the peptides of the present invention.

The branched, cyclical and straight chain peptides of Formulas I and II can be synthesized using any one of a number of conventional preparative and recovery methods, as will be readily apparent to one skilled in the art.

A preferable synthesis route for the straight chain, especially the smaller, peptides of the invention is the solid phase method. This method is well known in the art and is described, for example, in U.S. Pat. Nos. 4,683,291, 4,244,946, 4,305,872, and 4,316,891, and in Merrifield, *J. Am. Chem. Soc.*, 85, 2149 (1964), Vale et al, *Science*, 213, 1394–1397 (1981) and Marke et al, *J. Am. Chem. Sci.*, 103, 3178 (1981), the disclosures of which are incorporated herein by reference. Other preparative methods which may be employed include the processes of Houghten, *Proc. Natl. Acad. Sci.*, 82, 5132 (1985), the disclosures of which are also incorporated herein by reference. A preferable synthesis procedure particularly for the smaller branched or cyclical chain peptides, as a skilled artisan would recognize, would include conventional liquid phase processes. The liquid phase processes, as well as other synthesis methods, are described in *Principles of Peptide Synthesis*, M. Bodansky, ed. (Springer-Verlag, 1984), the disclosures of which are incorporated herein by reference. As would be apparent to one cognizant of the art, for larger peptides, a preferable procedure may include conventional recombinant DNA techniques. Such techniques are discussed in greater detail below. Recombinant techniques are well known and are described, for example, in Maniatis et al., *Molecular Cloning: A Laboratory Manual*, Cold Spring Harbor (1982), the disclosures of which are incorporated herein by reference.

Suitable recovery methods are described in the foregoing publications. Other recovery methods which may be employed include those described in Rivier et al., *Peptides: The Structure and Biological Function*, pp. 125–128 (1979), the disclosures of which are incorporated herein by reference.

The invention further provides compositions and methods for utilizing the subject compounds and compositions in inhibiting fibrinogen binding, platelet aggregation, and glycoprotein IIb-IIIa binding. The ability of the subject compounds to inhibit the foregoing activities makes them useful in inhibiting the physiological process of thrombosis. In addition, in light of their demonstrated activities, the compounds of the present invention may be employed in inhibiting cancer metastasis, an aberrant physiological phenomenon that is believed to require the adhesion of blood platelets to the cancer cells. The specificity of the subject compounds in carrying out these related functions makes them particularly useful as therapeutic and/or diagnostic agents.

In particular, the compositions of the present invention comprise an effective amount of a compound of Formula I and a physiologically acceptable carrier or diluent. Acceptable carriers or diluents for therapeutic, diagnostic or other uses are well-known in the pharmaceutical art, and are described, for example, in *Remington's Pharmaceutical Sciences*, Gennaro, A. R., ed. (Mack Publishing Co., Easton Pa., 1985).

In practicing the methods of the invention, the compounds or compositions can be used alone or in combination with one another, or in combination with other therapeutic or diagnostic agents. They can be utilized in vivo, ordinarily in a mammal, preferrably in a human, or in vitro. In employing in vitro, the compounds or compositions are applied to a cellular solution, that is, a solution containing the cellular component or components sought to be inhibited. In employing in vivo, the compounds or compositions can be administered to the mammal in a variety of ways, including parenterally, intravenously, subcutaneously, intramuscularly, colonically, rectally, nasally or intraperitoneally, employing a variety of dosage forms. As will be readily apparent to one skilled in the art, the useful in vivo dosage to be administered and the particular mode of administration will vary depending upon the age, weight and mammalian species treated, the particular compounds employed, and the specific use for which these compounds are employed. The determination of effective dosage levels, that is, the dosage levels necessary to achieve the desired result, will be well within the ambit of one skilled in the art. Typically, applications are commenced at lower dosage levels, with dosage being increased until the desired effect is achieved.

Antibodies, both monoclonal and polyclonal, directed to peptide compounds of the present invention are useful in isolation and identification of the subject proteins, and the present invention also pertains to such antibodies. To prepare the subject antibodies, any one of a number of techniques which known in the art can be employed. In one such technique, polyclonal antibodies may be synthesized by injecting an animal (for example, a rabbit) with one or more compounds of the invention. After injection, the animal naturally produces antibodies to these compounds. When the antibody level rises to a sufficient level, antibody-containing blood, called antiserum, is then drawn from the animal, and the compound-specific antibody is isolated from other antibodies in the antiserum by any one of a number of separation techniques (for example, affinity chromatography). Monoclonal antibodies may be prepared using the technique of Kohler and Milstein, *Nature* 256, pp. 495–497 (1975).

The invention further relates to nucleic acid, preferrably DNA, sequences which encode the peptide compounds of the present invention. Such fragments may be synthesized using standard nucleic acid synthesis techniques or, alternatively, may be obtained from genomic material of various sources using conventional genetic engineering protocol. One source of genomic material is the PAC1 hybridoma cell described in Shattil et al., *J. Biol. Chem.*, 260, 11107–11114 (1985), particularly the PAC1 -$\mu$ heavy chain variable region of that genome. Using standard recombinant DNA techniques, the nucleic acid sequences can be, if desired, incorporated into an appropriate cloning vector, transduced into an appropriate host cell and the proteins encoded by the nucleic acid fragment expressed and collected for further use, thereby providing a potentially convenient method for the production of the proteins, particularly the lengthy straight chain proteins, of the subject invention. Maniatis et al., *Molecular Cloning: A Laboratory Manual*, Cold Spring Harbor (1982), provides a detailed discussion of various recombinant DNA methodologies.

Cloning vector as used herein is defined as a DNA (or RNA) sequence, which allows the incorporation of specific experimental foreign DNA (or RNA), with the combined DNA (or RNA) being introduced into a host cell that can exist in a stable manner and express the protein dictated by the experimental DNA (or RNA). The foreign DNA (or RNA) combined with the vector DNA (or RNA) constitutes a recombinant DNA (or RNA) molecule which is derived from recombinant technology. Cloning vectors may include plasmids, bacteriophage, viruses and cosmids. Expression vectors are defined herein as DNA (or RNA) sequences that are required for the transcription of cloned copies of genes and the translation of their mRNAs in an appropriate host. Such vectors can be used to express either procaryotic or eucaryotic genes in a variety of cells such as bacteria, yeast, insect and mammalian cells. The proteins may also be expressed in a number of virus systems. An appropriately constructed expression vector should contain an origin of replication for autonomous replication in host cells, selective markets, a limited number of useful restriction enzyme sites, a high copy number, and strong promoters. A promoter is defined as a DNA (or RNA) sequence that directs RNA polymerase to bind to DNA and to initiate RNA synthesis. A strong promoter is one which causes mRNAs to be initiated at high frequency. Expression vectors may include, but are not limited to, cloning vectors, modified cloning vectors, specifically designed plasmids or viruses.

Finally, the present invention includes a peptide comprising an amino acid sequence corresponding to the amino acid sequence of the variable region of the μheavy chain of monoclonal antibody PAC1, as shown in FIG. 2, and any antibodies incorporating such sequence. The present invention further includes a peptide comprising an amino acid sequence corresponding to the amino acid sequence of the variable region of the μheavy chain of monoclonal antibody PAC1, as shown in FIG. 2, and an amino acid sequence corresponding to the amino acid sequence of the variable region of the κ light chain of monoclonal antibody PAC1, as shown in FIG. 1, and any antibodies incorporating such sequences. As will be apparent to those skilled in the art, and as described in the foregoing discussion on peptide synthesis using chemical and recombinant methodologies such as described in Riechmann et al., Nature, Vol. 332, pp. 323-327 (1988), various techniques are available to prepare such peptides. The recombinant DNA techniques can also be applied in the area of antibody manipulation. For a discussion of antibody engineering, see Riechmann et al., Nature, 332, 323-327 (1988), the disclosures of which are herein incorporated by reference.

Most preferrably, the invention is directed to monoclonal antibody PAC1. The hybridoma cell line producing this monoclonal antibody is described in Shattil et al., J. Biol. Chem., 260, 11107-11114 (1985), the disclosures of which are hereby incorporated by reference. Both the hybridoma cell PAC1 and the PAC1 monoclonal antibody produced therefrom are discussed in the Examples below. As with the peptides of Formulas I and II, the peptides and monoclonal antibodies of this paragraph are useful as inhibitors of fibrinogen binding, platelet aggregation, and/or glycoprotein IIb-IIIa binding, and, similarly, are effective in the treatment of certain physiological conditions, such as thrombosis and/or cancer metastasis, and the present invention is further directed to these uses.

The invention is further described in the following Examples. These Examples are not to be construed as limiting the scope of the appended Claims.

EXAMPLES

Example 1

Cell Culture and Isolation of mRNA

PAC1 hybridoma cells, prepared as described in Shattil et al., J. Biol. Chem., 260, 11107-11114 (1985), were grown in a standard culture medium containing fetal calf serum, and $5 \times 10^8$ cells were harvested and resuspended in 4M guanidine thiocyanate as described in Chirgwin et al., Biochemistry, 18, 5294-5299 (1979). Total RNA was isolated after centrifugation through a CsCl cushion and poly A+RNA was isolated using oligodT cellulose following the procedures set forth in Aviv et al., Proc. Natl. Acad. Sci., U.S.A., 69, 264-268 (1972).

Example 2

Sequencing of PAC1 Immunglobulin Variable Regions

Using complementary oligonucleotide primers from the 5' region of the mouse μ and κ constant region mRNAs, (5'-GCTCTCGCAGGAGACGAG and 5'-GGTGGGAAGATGGATACAGTT, respectively), the sequences of PAC1-μ (light chain) and κ (heavy chain) mRNAs were determined using the direct dideoxy chain termination method as described by Geliebter in Focus, 9, 1,5-8 (1987). Briefly, 20 ng of end-labeled primers were annealed to 10 μg of poly A+mRNA at 50° C. and primers were extended in the presence of dideoxynucleotides and reverse transcriptase. The products of this reaction were electrophoresed on 6% denaturing polyacrylamide gels that were then exposed to autoradiography. Once approximately 200 bp of sequence had been determined, complementary primers within the variable region about 150 bp upstream of the constant region were synthesized in order to extend the sequence further 5' within the variable region. The primer used in the PAC1 -μ reaction was 5'-CATTAGCTTGCAGACTGTTC and in the PAC1 -κ reaction was 5'-ATCTTGAGTGTGAAATCTGT. A small portion, about 50 nucleotides, of the 3' end of the κ mRNA was determined using the modified Maxam and Gilbert technique of Schlomchik et al., J. Exp. Med., 164, 407-427 (1986). FIG. 1 shows the nucleotide sequence of the variable region of the κ light chain of a PAC1 hybridoma cell, along with the predicted amino acid sequence. FIG. 2 shows the nucleotide sequence of the variable region of the μ heavy chain of a PAC1 hybridoma cell, along with the predicted amino acid sequence. In both FIGS. 1 and 2, the complimentary determining regions (CDRs) are shown in boxes. The amino acids numbered according to convention. Kabat E. A., Wu, T. T., Reid-Miller, M., Perry, H. M., Gottesman, K. S., Sequences of Proteins of Immunologic Interest (US DHHS, PHS, NIH 1987).

Example 3

Peptide Synthesis and Analysis

The peptide NH$_2$-Ala-Arg-Arg-Ser-Pro-Ser-Tyr-Tyr-Arg-Tyr-Asp-Gly-Ala-Gly-Pro-Tyr-Tyr-Ala-Met-Asp-Tyr-COOH, which corresponds to amino acids 93 through 102 of the PAC1 -μ variable region (FIG. 2) and which is referred to herein as the Arg-Tyr-Asp-21mer, and various other peptides used herein were synthesized by the solid phase method using an Applied Biosystems Inc. 430A automated synthesizer. Boc-amino acids supplied by the manufacturer were used except for Boc-Asp (Chx). Triple couplings were used for Arg$^9$, Ser$^4$, Tyr$^7$, Tyr$^8$, Arg$^3$, Arg$^2$, and Ala$^1$ of the Arg-Tyr-Asp-21mer. The remaining residues were incorporated by a double coupling protocol. The peptides were cleaved from the solid support by the Sn2/Sn1 HF cleavage procedure described in Tam, J. Amer. Chem. Soc., 105, 6442-6455 (1983) and purified by gel filtration (Sephadex G-50F, 50% HOAc) and reverse phase HPLC (Vydac C18, 15μ, 5×30 cm column, 95% A-B to 75% A-B over 60 minutes at a flow rate of 100 ml/min; A=0.1% TFA-H$_2$O, B=0.1% TFA-CH$_3$CN). Products were characterized by amino acid analyses after acid hydrolysis, fast atom bombardment mass spectrometry (FABMS), nuclear magnetic resonance spectroscopy, and sequence analysis after Edman degradation. Analyses were consistent with the expected structures, with a product purity of ≧95%.

Example 4

Binding of PAC1 and Fibrinogen to Platelets

The binding of PAC1 monoclonal antibody and fibrinogen to gel-filtered human blood platelets was examined by fluorescence-activated flow cytometry using the procedures of Shattil et al., *Blood*, 70, 307–315 (1987). Venous blood from normal donors was drawn into 1/7 vol of NIH formula A acid-citrate-dextrose solution, platelet-rich plasma was obtained, and the platelets were gel-filtered into an isotonic HEPES-containing buffer at pH 7.4, as described in Shattil et al., *Blood*, 68, 1224–1231 (1986). To examine the effect of synthetic peptides on PAC1 binding to activated platelets, $5 \times 10^7$ platelets were incubated for 15 min at room temperature in a final vol of 50 μl in the presence of varying concentrations of (0–100 μM) of peptide, 40 μg/ml fluorescein-labeled PAC1 (FITC-PAC1 ), 10 μM ADP and 10 μM epinephrine. Then, 500 μl of the isotonic buffer was added and antibody binding was quantitated using a flow cytometer, as described in Shattil et al., *Blood*, 70, 307–315 (1987). Fibrinogen binding to platelets was measured using the same incubation system, except that 50 μg/ml of purified human fibrinogen as described in Bennett et al., *J. Clin. Invest.*, 64, 1393–1400 (1979) was added and the monoclonal antibody, FITC-9F9, was used instead of FITC-PAC1. Antibody 9F9 is specific for fibrinogen and has been used successfully to measure the amount of fibrinogen bound to platelets. Abrams et al., *Blood*, 70, 335a (1987). Previous studies have established that the amount of FITC-labeled antibody bound to platelets determined by flow cytometry is related in a linear fashion to the amount of antibody bound determined in a conventional radioligand binding assay. Shattil et al., *Blood* 70, 307–315 (1987). The amount of platelet-bound FITC-PAC1 or FITC-9F9 was determined by analyzing 10,000 platelets for the extent of fluorescence at 488 nm, and binding expressed as the mean fluorescence intensity in arbitrary fluorescence units.

Under these conditions, the Arg-Tyr-Asp-21mer peptide inhibited the binding of FITC-PAC1 to platelets with an $IC_{50}$ of 20–30 μM (as shown in FIG. 3A, filled circles). This was similar to the $IC_{50}$ of the tetrapeptide, $NH_2$-Arg-Gly-Asp-Ser-COOH (Arg-Gly-Asp-Ser) (FIG. 3A, unfilled circle). In five separate experiments, Dixon plot analysis carried out in accordance with Segel, Enzyme Kinetics 465–504 Wiley-Interscience, N.Y. (1975), revealed that the apparent Ki for inhibition of PAC1 binding by Arg-Tyr-Asp-21mer was 10.2±4.3 μM (SE). As a control, an unrelated peptide of similar length having the sequence $NH_2$-Tyr-Val-Asp-Gly-Asp-Gln-Cys-(Acm)-Glu-Ser-Asn-Pro-Cys-Leu-Asn-Gly-Gly-Met(O)-Cys-(Acm)-Lys-Asp-Asp-Ile-Asn-Ser-Tyr-Gly-Cys-Phe-COOH (unrelated-28mer)(control) had no effect on FITC-PAC1 binding (FIG. 3A, unfilled squares). Identical results were obtained when platelets were activated with phorbol myristate acetate instead of ADP and epinephrine (data not shown).

Figure 3B:
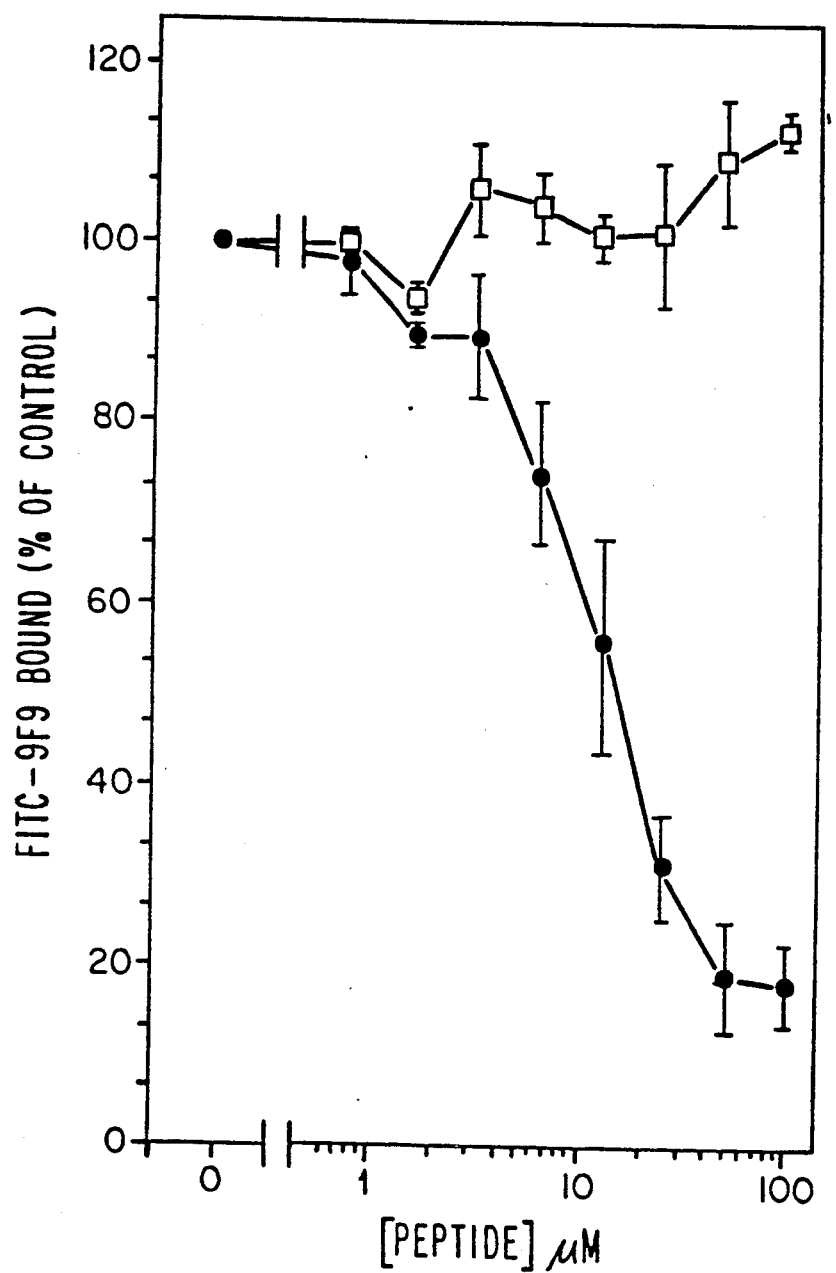

The ability of Arg-Tyr-Asp-21mer to inhibit fibrinogen binding to activated platelets was also tested. Fibrinogen binding was assessed by flow cytometry using a FITC-labeled anti-fibrinogen monoclonal antibody, 9F9. When platelets were activated with ADP plus epinephrine in the presence of 50 μg/ml of fibrinogen, Arg-Tyr-Asp-21mer inhibited fibrinogen binding with an $IC_{50}$ of μM (FIG. 3B, filled circle). The control peptide (unrelated 28mer) had no effect on 9F9 binding (FIG. 3B, unfilled square). In three experiments, Dixon plot analysis showed that this peptide inhibited fibrinogen binding with an apparent Ki of 5.5±3.5 μM.

Figure 4:
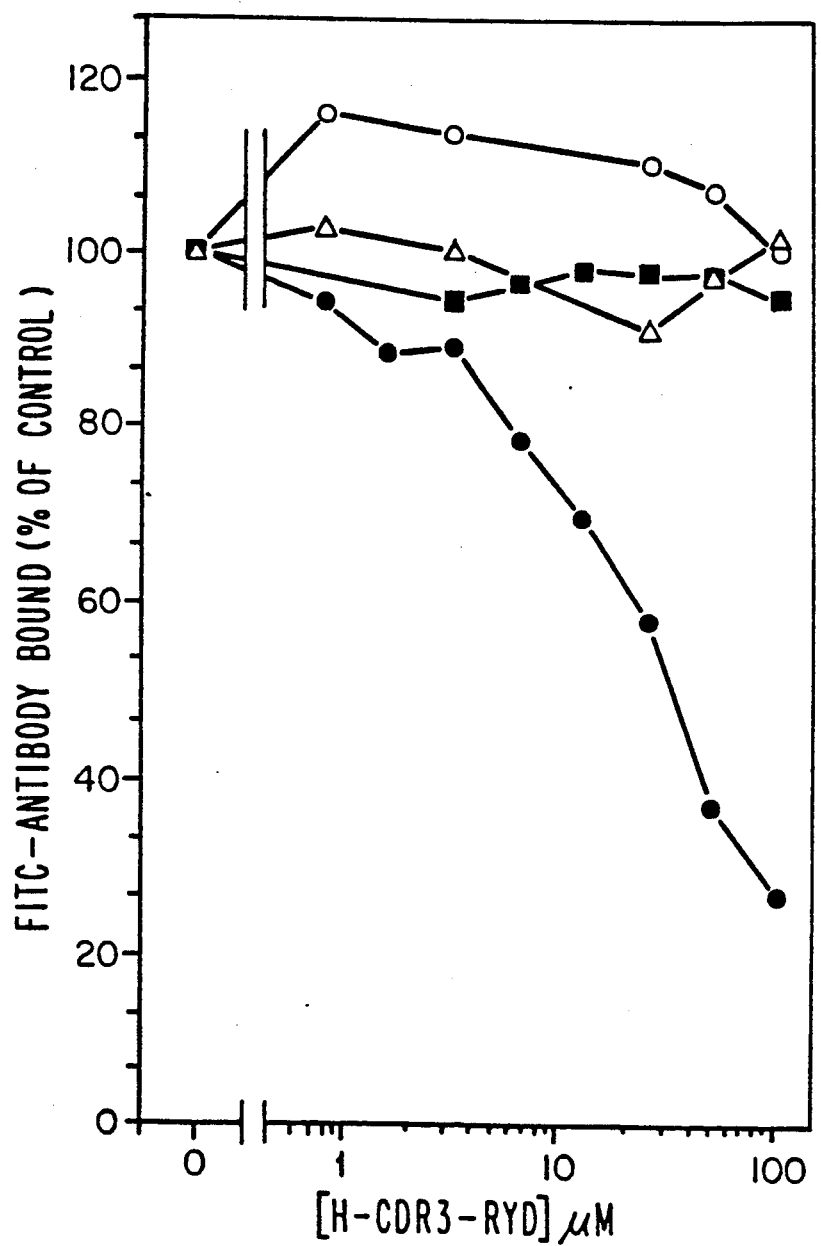
FIG. 4 shows the effect of the Arg-Tyr-Asp-21mer peptide on the binding of various monoclonal antibodies to platelets. Gel-filtered platelets were incubated in the presence of Arg-Tyr-Asp-21mer and various FITC-labeled anti-platelet monoclonal antibodies. Monoclonal antibody binding was determined by flow cytometry. In the case of antibody AP1 (specific for platelet glycoprotein Ib) (unfilled circles), the platelets were not activated. In the case of antibodies PAC1 (specific for activated glycoproteins IIb-IIIa) (filled circles), BIB5 (specific for glycoprotein IIb) (filled squares) and S12 (specific for GMP-140) (unfilled triangles), the platelets were activated with ADP and epinephrine (10 μM each). The data shown are from a single experiment representative of two runs performed as described.

To examine the specificity of the Arg-Tyr-Asp-21mer peptide in inhibiting PAC1 monoclonal antibody binding, the effect of this peptide on the binding of monoclonal antibodies to other platelet glycoproteins were examined. The Arg-Tyr-Asp-21mer peptide had no effect on the binding of FITC-API to platelet glycoprotein Ib on resting platelets (FIG. 4, unfilled circles). In addition, the peptide had no effect on the binding of either FITC-B1B5 to glycoprotein IIb or of FITC-S12 to GMP-140 on activated platelets (FIG. 4, filled squares and unfilled triangles, respectively). The peptide had a marked effect on PAC1 binding (FIG. 4, filled circles). Antibody S12, described in McEver et al., *J. Biol. Chem.*, 259: 9799 (1984) specific for an α-granule membrane protein (GMP) expressed on the surface of activitated platelets. Antibody B1B5 is specific for glycoprotein IIb, and is discussed in Shattil, *J. Biol. Chem.*, 260, 11107–11114 (1985) and Bennett et al., *Proc. Natl. Acad. Sci., U.S.A.*, 80, 2417–2421 (1983).

Example 5

Platelet Aggregation Studies

The Effect of Arg-Tyr-Asp-21mer peptide on blood platelet aggregation was examined. The aggregation of gel-filtered platelets was carried out as described in Shattil et al., *Blood*, 68, 1224–1231 (1986). Platelets ($2 \times 10^8$/ml) were stirred at 37° C. in the presence of human fibrinogen (100 μg/ml) and $CaCl_2$ (1 mM) and aggregation was initiated by the addition of 10 μM ADP. Aggregation was monitored as a change in light transmittance, and is expressed as the initial rate of aggregation.

Figure 5:
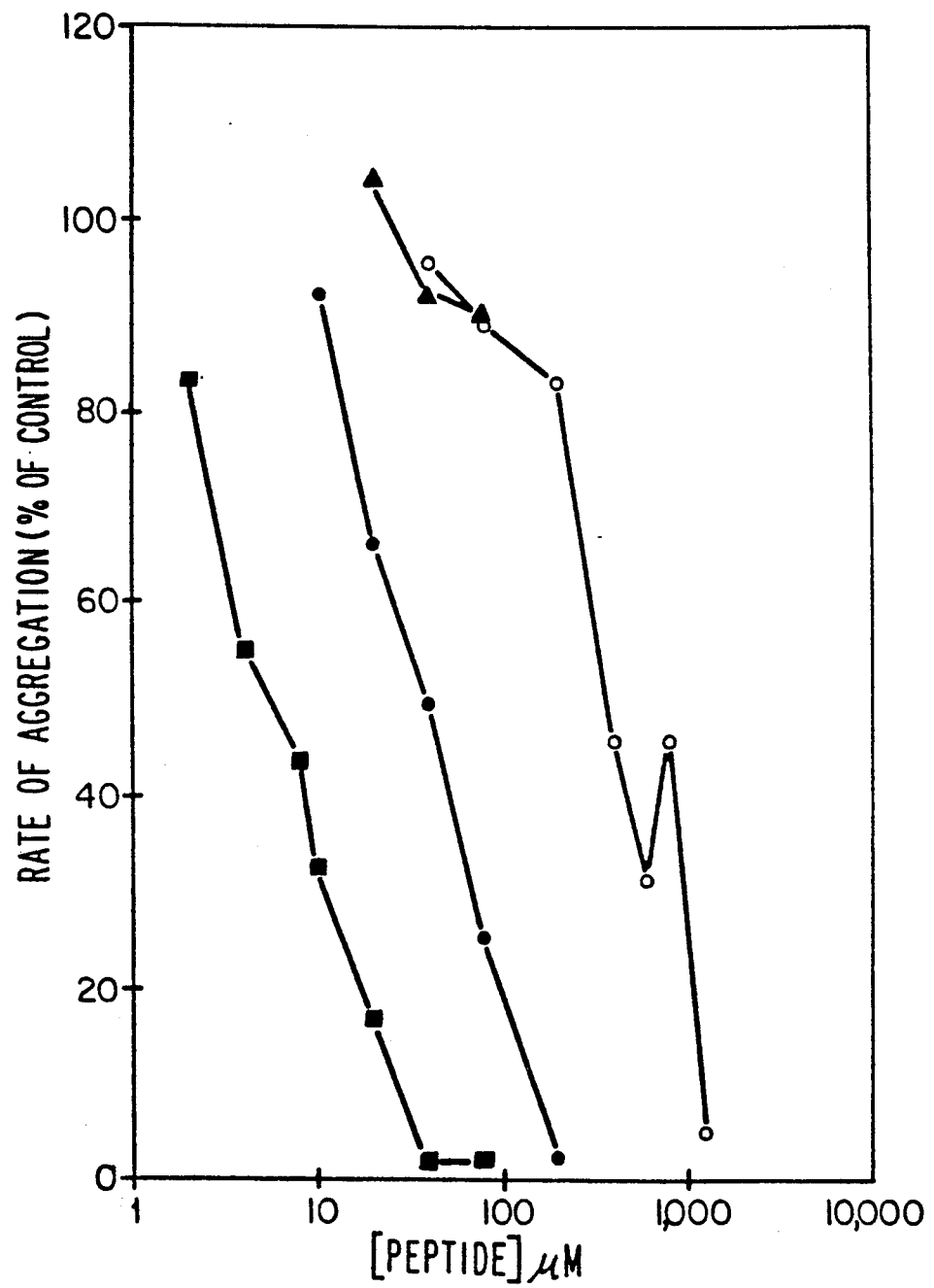
FIG. 5 shows the effect of Arg-Tyr-Asp-21mer on platelet aggregation. Gel-filtered platelets were stirred for 3 min in an aggregometer cuvette in the presence of ADP (10 μM), fibrinogen (100 μg/ml), CaCl₂ (1 mM), and one of the following: Arg-Tyr-Asp-21mer (filled circles); Arg-Tyr-Asp-21mer having a Gly substituted for the Tyr residue (Arg-Gly-Asp-21mer) (filled squares); Arg-Tyr-Asp-21mer having the Asp and Arg residues reversed (Asp-Tyr-Arg-21mer) (filled triangles); or Arg-Tyr-Asp-21mer having a d-Ala residue substituted for the Tyr residue (Arg-d-Ala-Asp-21mer) (unfilled circles). Aggregation is expressed as the initial rate of aggregation, where the rate of aggregation in the absence of added peptide is arbitrarily denoted as 100%. The data represent the means of three separate experiments performed as described.

In three experiments Arg-Tyr-Asp-21mer inhibited the initial rate of ADP-induced platelet aggregation with an $IC_{50}$ of approximately 40 μM (FIG. 5, filled circles). At 10 μg/ml fibrinogen the $IC_{50}$ was approximately 10 μM (data not shown).

Example 6

Figure 6A:
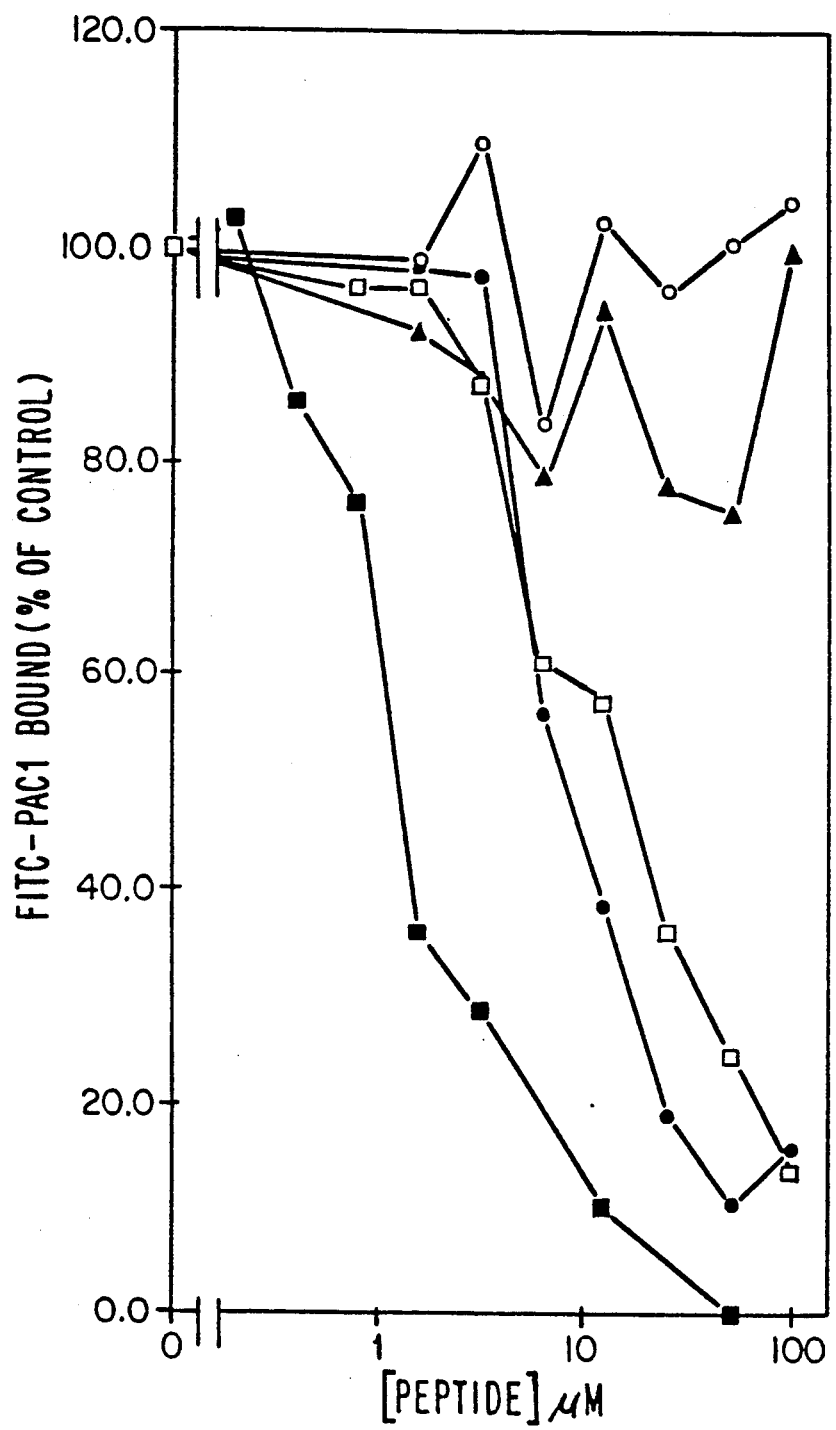
FIG. 6 shows the effect of Arg-Tyr-Asp on the binding of FITC-PAC1 (FIG. 6A) or FITC-9F9 (FIG. 6B) and fibrinogen to platelets stimulated with ADP and epinephrine (10 μM each). The specific peptides tested were Arg-Tyr-Asp-21mer (filled circles), Arg-Gly-Asp-21mer (filled squares), Asp-Tyr-Arg-21mer (filled triangles), Arg-d-Ala-Asp-21mer (unfilled circles) or Arg-Gly-Asp-Ser (unfilled squares). The conditions in each of the binding assays were identical to those in FIG. 3. Data shown are from a single experiment representative of three runs performed as described.
Figure 6B:
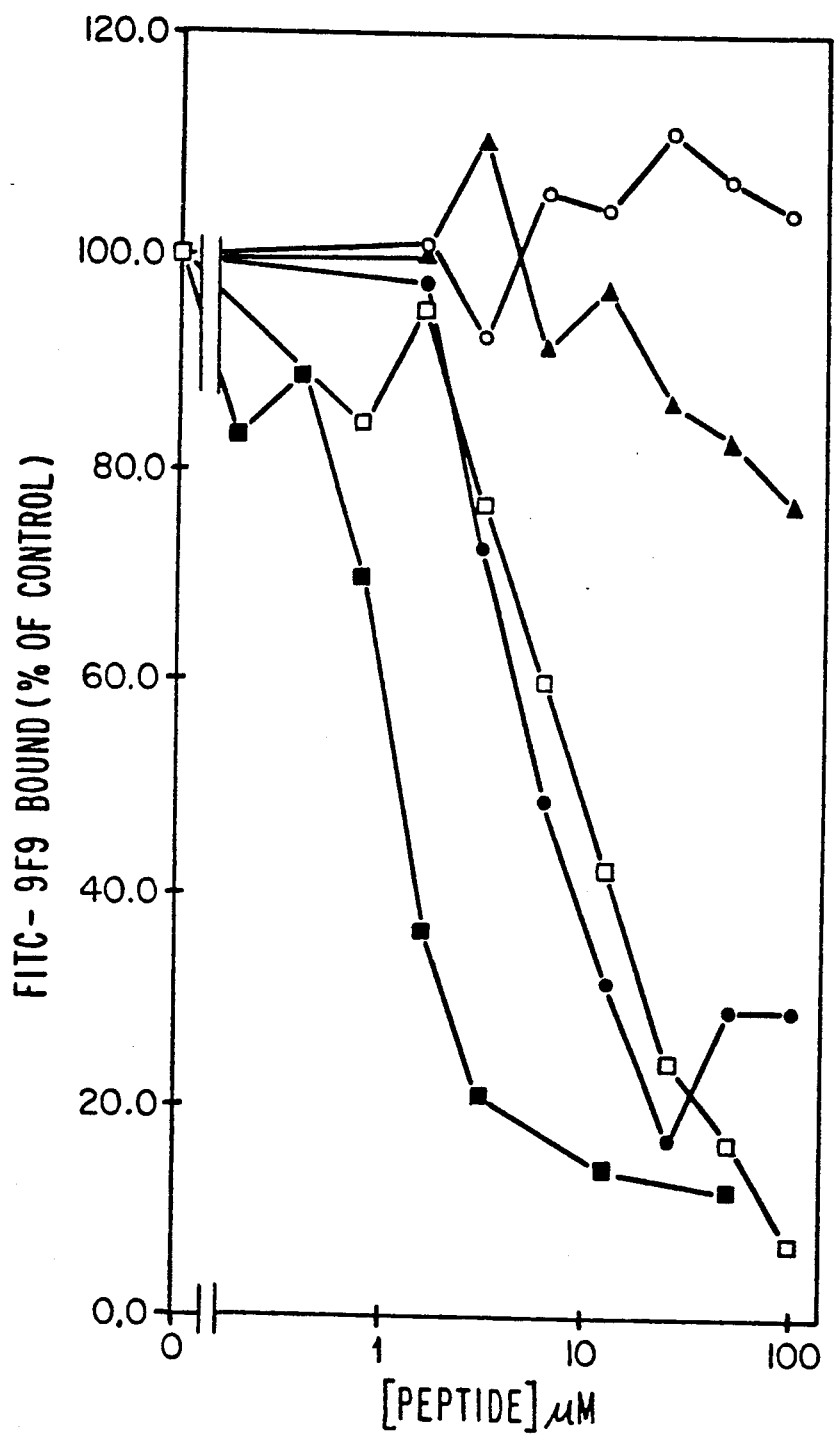

The specific role of the Arg-Tyr-Asp sequence within Arg-Tyr-Asp-21mer was examined by testing three additional peptides identical to the Arg-Tyr-Asp-21mer except for specific modifications in the Arg-Tyr-Asp region. Substitution of the tyrosine in Arg-Tyr-Asp with glycine to produce an Arg-Gly-Asp-21mer increased the inhibitory potency of the peptide by about ten-fold in both the aggregation assay (Arg-Gly-Asp-21mer, FIG. 5, filled squares; Arg-Tyr-Asp-21mer, FIG. 5, filled circles) and the PAC1 and fibrinogen binding assays (Arg-Tyr-Asp-21mer, FIG. 6, filled squares; Arg-Tyr-Asp-21mer, FIG. 6, filled squares). On the other hand, substitution of the tyrosine with a D-alanine to produce an Arg-D-Ala-Asp-21mer, or inversion of the Arg and Asp residues to produce an Arg-Tyr-Asp-21mer substantially reduced the inhibitory capacity of the peptide (Arg-d-Ala-Asp-21mer, FIG. 6, unfilled circles; Asp-Tyr-Arg-21mer, FIG. 6, filled triangles). The Arg-Gly-Asp-Ser-tetramer is shown in FIG. 6 as the unfilled square.

These specific modifications of the Arg-Tyr-Asp sequence within the Arg-Tyr-Asp-21mer peptide clearly establish that this sequence of three amino acids is of significance to the functional properties of the entire peptide.

Various modifications of the invention in addition to those shown and described herein will be apparent to those skilled in the art from the foregoing description. Such modifications are also intended to fall within the scope of the appended Claims.

What is claimed is:

1. A compound of the formula $$R^1\text{-}(X^1)_n\text{-}Arg\text{-}Tyr\text{-}Asp\text{-}(X^2)_m\text{-}R^2$$

or physiologically acceptable salts thereof, wherein
  $X^1$ is Ala-Arg-Arg-Ser-Pro-Ser-Tyr-Tyr;
  $X^2$ is Gly-Ala-Gly-Pro-Tyr-Tyr-Ala-Met-Asp-Tyr;
  m is 1;
  n is 1;
  $R^1$ is a protected or unprotected terminal amino group; and
  $R^2$ is a protected or unprotected terminal carboxy group.

2. A compound of claim 1 wherein
  $R^1$ is an unprotected terminal amino group; and
  $R^2$ is an unprotected terminal carboxyl group.

3. A composition comprising an effective amount for inhibiting fibrinogen binding of a compound of claim 1 and a physiologically acceptable carrier or diluent.

4. A composition comprising an effective amount for inhibiting platelet aggregation of a compound of claim 1 and a physiologically acceptable carrier or diluent.

5. A composition comprising an effective amount for inhibiting thrombosis of a compound of claim 1 and a physiologically acceptable carrier or diluent.

6. A composition comprising an effective amount for inhibiting binding of a substance to a blood platelet membrane glycoprotein IIb-IIIa complex of compound of claim 1 and a physiologically acceptable carrier or diluent.

* * * * *

UNITED STATES PATENT AND TRADEMARK OFFICE
CERTIFICATE OF CORRECTION

PATENT NO. : 5,169,836
DATED : December 8, 1992
INVENTOR(S) : Shattil et al

Page 1 of 2

It is certified that error appears in the above-identified patent and that said Letters Patent is hereby corrected as shown below:

Column 2, lines 22-23, should appear as follows:

--$R^1_2$ is a protected or unprotected terminal amino group; $R^2$ is a protected or unprotected terminal carboxy group.--;

Column 3, line 59, delete "BIB5" and insert therefor --B1B5--;

Column 4, line 62, delete "o" and insert therefor --or--;

Column 8, line 25, after "Ile" 2nd Occurrence" --Ser-Lys-Asp-Asn-Ser-Lys-Ser-Gln-Val-Phe-Phe-Lys--;

Column 13, line 6, delete "Fibrinooen" and insert therefor --Fibrinogen--;

UNITED STATES PATENT AND TRADEMARK OFFICE
CERTIFICATE OF CORRECTION

PATENT NO. : 5,169,836

DATED : December 8, 1992

INVENTOR(S) : Shattil et al

It is certified that error appears in the above-identified patent and that said Letters Patent is hereby corrected as shown below:

Column 14, line 12,           delete "FITC-API" and insert therefor --FITC-AP1--;

Column 14, after line 46, please insert --Modifications in the Arg-Tyr-Asp Sequence of the 21mer Peptide --;

Column 14, line 60,           delete "Arg-D-Ala-Asp-21mer" and insert therefor --Arg-d-Ala-Asp-21mer--.

Signed and Sealed this

Sixteenth Day of November, 1993

*Attest:*

*Attesting Officer*

BRUCE LEHMAN

*Commissioner of Patents and Trademarks*